United States Patent [19]
Ross et al.

[11] Patent Number: 5,994,071
[45] Date of Patent: Nov. 30, 1999

[54] ASSESSMENT OF PROSTATE CANCER

[75] Inventors: Jeffrey S. Ross, New Lebanon, N.Y.; Patrick J. Muraca, Frederick, Md.

[73] Assignees: Albany Medical College, Albany, N.Y.; Ventana Medical Systems, Inc., Tucson, Ariz.

[21] Appl. No.: 08/832,745

[22] Filed: Apr. 4, 1997

[51] Int. Cl.⁶ .............................. C12Q 1/68; C12P 19/34; G01N 33/48; C07H 21/02

[52] U.S. Cl. ................................ 435/6; 435/91.2; 436/64; 436/813; 536/23.1; 536/24.3; 536/24.31; 536/24.53

[58] Field of Search ........................ 435/6, 91.2; 436/64, 436/813; 536/24.3, 24.31, 24.33, 23.1

[56] References Cited

U.S. PATENT DOCUMENTS

| | | | |
|---|---|---|---|
| 5,616,731 | 4/1997 | Lobberding et al. | 549/282 |
| 5,658,730 | 9/1997 | McGill et al. | 435/6 |
| 5,705,157 | 1/1998 | Greene | 424/138.1 |

OTHER PUBLICATIONS

Matthews et al, "Analytical Strategies for the useof DNA probes", Anal. Biochem. 169:1–25, 1988.

Descotes et al, "Human Breast Cancer: Correlation study between HER–2/neu amplification and prognostic factors in an unselected population", Anticancer Res. 13:119–124, 1993.

Naraghi et al, "Human prostate cancer overexpression of ErbB2 may be due to HER2/neu gene amplification", Proceedings American Association for Cancer Research 36:A3838, Mar. 1995.

Myers et al, "Serum levels of erbB–2 protein in prostate adenocarcinoma", Proceedings American Association for Cancer research 36:A3838, Mar. 1995.

Paterson et al, "Correlation between c–erbB–2 amplification and risk of ecurrent disease in node–negative breast cancer", Cancer Res. 51:556–567, Jan. 1991.

Ross, J.S., et al.,: Contribution of HER–2/neu Oncogene Expression to Tumor Grade and DNA Content Analysis in the Predication of Prostatic Carcinoma Metastasis. ancer. vol. 72, No. 10, pp. 3020–3028: Nov. 15, 1993.

Kuhn, E.J., et al.,: Expression of the c–erbB–2 (HER–2/neu) Oncoprotein in Human Prostatic Carcinoma. The Journal of Urology. vol. 150, pp. 1427–1433: Nov. 1993.

Ware, J.L., et al.,: Immunohistochemical Detection of c–erbB–2 Protein in Human Benign and Neoplastic Prostate. Human Pathology. vol. 22, No. 3, pp. 254–258: Mar. 1991.

Battifor, H., et al.,: Immunohistochemical Assay of neu/ c–erbB–2 Oncogene Product in Paraffin–embedded Tissues in Early Brest CancerRetrospective Follow–up Study of 245 Stage I and II cases. Modern Pathology. vol. 4, No. 4, pp. 466–474: 1991.

Sadasivan, R., et al.,: Overexpression of HER–2/neu may be an indicator of Poor Prognosis in Prostate Cancer. The Journal of Urology. vol. 150, pp. 126–131: Jul. 1994.

Takahashi, S., et al.,: Potential Markers of Prostate Cancer Aggressiveness Detected by Fluorescence In Situ Hybridization in Needle Biopsies. Cancer Research. vol. 54, pp. 3574–3579: Jul. 1, 1994.

Xiao, S., et al.,: Novel Fluorescence in Situ Hybridization Approaches in Solid Tumors—Characterization of Frozen Specimens, Touch Preparation, and Cytological Preparations. American Journal of Pathology, vol. 147, No. 4, pp. 896–904: Oct. 1995.

ian, J., et al.,: Chromosomal Anomalies in Prostatic Intraepithelial Neoplasia and Carcinoma Detected by Fluorescence in Situ Hybridization. Cancer research. vol. 55, pp. 5408–5414: Nov. 15, 1995.

Brown, J.A., et al.,: Chromosomal Aneusomies Detected by Fluorescent In Situ Hybridization Analysis in Clinically Localized Prostate Carcinoma. The Journal of Urology. vol. 152, pp. 1157–1192: Oct. 1994.

Visakorpi, T., et al.,: Expression of Epidermal Growth Factor Receptor and ERBB2 (HER–2/Neu) Oncoprotein in Prostatic Carcinomas. Modern Pathoogy. vol. 5, No. 6, pp. 643–648: 1992.

Zitzelsberger, H., et al.,: Numerical Abnormalities of Chromosome 7 in Human Prostate Cancer Detected by Fluorescence In Situ Hybridization (FISH) on Paraffin–Embedded Tissue Sections with Centromere–specific DNA Probes. Journal of Pathology. vol. 172, pp. 325–335: 1994.

Latil, Fournier G., et al.,: Gene Amplification in Advanced– Stage Human Prostate Cancer. Urol Res. vol. 22, No. 6, pp. 343–347: 1995.

Lyne, J.C., et al.,: Tissue Expression of neu Differentaition Factor/Heregulin and its Receptor Complex in Prostate Cancer and its Biological Effects on Prostate Cancer Cells In Vitro. Cancer Journal From Scientific American. vol. 3 No. 1, pp. 21–30: 1997.

Muller, P., et al.,: Detection of Genetic Alterations in Micrometastic Cells in Bone Marrow of Cancer Patients by Fluorescence In Situ Hybridization. Cancer Genetics & Cytogenetics. vol. 88 No. 1, pp. 8–16: 1996.

Veltri, R.W., et al.,: Abnormal Expression of a Truncated Intracellular HER–2/neu mRNA in Prostate Cancer. Proc. Annu Meet Am Assoc. Cancer Res., vol. 37, p. A572: 1996.

Zhau, H.E., et al.,: Biomarkers Associated with Prostate Cancer Progression. Journal of Cellular Biochemistry. Supplement, vol. 19, pp. 208–216: 1994.

*Primary Examiner*—Jeffrey Fredman
*Attorney, Agent, or Firm*—Jonathan M. Cohan; John E. Tarcza

[57] ABSTRACT

A method of determining the severity of prostatic cancer includes measuring the level of amplification of the HER-2/neu gene in a sample of prostate tissue by fluorescence in-situ hybridization and comparing the measured level of amplification of the HER-2/neu gene in the sample with the level of HER-2/neu gene in normal prostate tissue. A method for determining treatment for a patient afflicted with prostate cancer includes determining whether the number of copies of HER-2/neu gene in prostate cells from the patient exceeds four by using fluorescence in-situ hybridization and aggressively treating such patient having prostate cells with five or more copies of the HER-2/neu gene.

9 Claims, 3 Drawing Sheets

ASSESSMENT OF PROSTATE CANCER

BACKGROUND

1. Field of the Invention

The present invention relates to treatment of neoplastic disease and more particularly to determining severity of prostate cancer in afflicted patients.

2. Description of Related Art

The ability to monitor neoplastic disease status is an important tool in cancer therapy. In addition to improving prognostication, knowledge of the disease status allows an attending physician to select the most appropriate course of therapy. For example, patients with a high likelihood of relapse can be treated aggressively with powerful systemic chemotherapy and/or radiation therapy. Where there is a lesser likelihood of relapse, less aggressive therapies can be chosen. Since severe patient distress can be caused by more aggressive therapy regimens, it is desirable to determine which patients require such aggressive therapies.

Prostate cancer disease is responsible for nearly 3% of all deaths in men over the age of 55 years. It is likely that more than 300,000 new cases of prostate cancer will be diagnosed in American men this year. Prostate cancer has variable clinical outcome and recent studies indicating the potential benefits of withholding therapy in older men with limited disease and the potential to predict inoperable cancer in men with aggressive tumors has prompted the search for new prognostic markers that could be applied to the initial guided prostate needle biopsy and prove successful in selecting therapy and predicting disease outcome.

The identification of new prognostic markers in prostate cancer would allow urologists to stratify their patients into groups that could receive significantly different therapies. Tumor grade and DNA ploidy have been generally accepted as significant predictors of outcome for the disease (see e.g., Ross et al., Cancer, 74:2811–18(1994)), but a clearly established prognostic panel capable of defining therapy selection has not emerged to date.

Fluorescence in-situ hybridization (FISH) has recently been employed in detection of chromosomal aneusomies and gene copy numbers in both solid tumors and hematopoietic malignancies. See, e.g., Wolman SR., Pathology Annual, Appelton and Lang, Stanford, Conn., pp.227–244 (1995). Using chromosome specific probe, FISH was found to be more sensitive than flow cytometry for the detection of aneuploidy in prostate cancer. Visacorpi et al., Am J Pathol, 145:624–630 (1994). High grade prostate cancer has been linked to chromosomal aneusomy by FISH and chromosome 8 aneusomy has been associated with increased tumor stage. Brown et al., J Urol, 152:1157–1162 (1994). FISH detected aneusomy in prostate cancer has been associated with recurrent and progressive disease. See Lifson et al., Anal Quant Cytol Histol, 17:93–99 (1995); Koivisto et al., Am J. Pathol, 147:16–8–14 (1995); Lieber M M., J Cell Biochem (suppl), 19:246–248 (1994); Bandyk et al., Genes Chrom Cancer, 9:19–27 (1994); Zitzelsberger et al., J Pathol, 172:325–335 (1994); Alcaraz et al., Cancer Res, 54: 3998–4002 (1994). Studies have revealed varying abnormalities associated with disease progression including increased copy number of chromosome X (Koivisto et al., supra) and aneusomies of chromosome 7 and/or 8 (Lieber M M., supra; Bandyk et al., supra; Zitzelsberger et al., supra; Alcaraz et al., supra). FISH based techniques have also been utilized recently to demonstrate potential candidate tumor suppressor genes that may prove of significance in prostate cancer. Ziao et al., Am J Pathol, 147:896–904 (1995); Cher, J Urol, 153:249–254 (1995).

The HER-2/neu (c-erbB2) gene is localized to chromosome 17p and encodes a transmembrane tyrosine kinase growth factor receptor with substantial homology to the epidermal growth factor receptor. HER-2/neu expression in breast cancer has generally been accepted as a predictor of disease outcome with HER-2/neu gene amplification by southern analysis and corresponding overexpression of HER-2/neu protein ($p185_{neu}$) by western blotting or immunohistochemistry (IHC) predicting early disease relapse in lymph node negative and lymph node positive patients. See Battifora et al., Modern Pathol, (1991) 4:466–474; Press et al., Cancer Res, (1993)53:4960–4970; Seshadri et al., Clin Oncol, (1993)11:1936–1942; Descotes et al., Anticancer Res, (1993) 13:119–124; Muss et al., N Engl J Med, (1994) 330:1260–1266; Tetu et al., Cancer, (1994) 73:2359–2365; Marks et al., Annal Surg, (1994) 219:332–341. Recently, amplification of the HER-2/neu gene or overexpression of the HER-2/neu protein have been clinically utilized to identify patients likely to be refractory to less intense cytotoxic chemotherapy in breast cancer. Muss et al., supra. Moreover, clinical trials featuring patients with HER-2/neu amplified tumors and therapeutic use of an administered antibody to HER-2/neu protein have shown promise for the treatment of refractory metastic ovarian and breast cancer. See Baselga et al., J Clin Oncol, 14(3):737–44 (1996); Peitras et al., Oncogene, 9(7): 1829–1838 (1994).

In prostate cancer, a consensus as to the predictive value of HER-2/neu gene amplification and $p185_{neu}$ protein expression has not been reached. The majority of published prognostic studies of HER-2/neu status in prostate cancer have utilized immunohistochemical techniques featuring a variety of antibodies with differing sensitivities and specificities particularly when utilized in archival specimens. See, e.g., Visacorpi et al., Modern Pathol, (1992) 5:643–648; Ibrihlm et al., Surg Oncol, (1992) 1:151–155; Ross et al., Cancer, (1993)72:3020–3028; Sadasivan et al., J Urol, (1993) 150:126–131; Kuhn et al., J Urol, (1993) 150:1427–1433; Melon et al., J Urol, (1992) 147:496–499. Molecular based studies of the HER-2/neu gene in prostate cancer have been limited to two published reports from one research group which reported an absence of gene amplification by Southern analysis in a small number of prostate cancer specimens, i.e., Latil et al., Int J Cancer, (1994) 59:637–638; Fournier et al., Urol Res, (1995) 22:343–347. In one report using the MAB-1 antibody, no staining could be identified on archival fixed tissue specimens. Visacorpi et al., Modern Path., supra. In another study, immunoreactivity for HER-2/neu oncoprotein was more intense in prostatic hyperplasia and prostatic intraepithelial neoplasia than in adenocarcinoma. Ibrihlm et al., supra. Several previously published immunohistochemical studies of HER-2/neu in prostate cancer have failed to link expression with disease outcome. In one study using the paB-1 antibody on formalin-fixed paraffin-embedded archival material, HER-2/neu oncoprotein expression was identified in one of clinically localized prostate cancers, but did not appear to be a significant prognostic marker. See Kuhn et al., supra. A significant decrease of EGF receptor and increase immunodetection for HER-2/neu protein was identified in prostate cancer but the findings did not correlate with tumor stage or grade. See Melon et al., supra. Finally, in a more recent study of prostate cancer and benign prostatic hyperplasia using the AB-3 antibody on archival tissues, $p185_{neu}$ immunostaining did not correlate with Gleason grade and a trend toward an inverse relationship was presented. See Gu et al., Cancer Letters, (1996) 99:185–189.

Several immunohistochemical studies of HER-2/neu protein expression in prostate cancer have correlated with other prognostic variables and suggested correlation with disease outcome. In one study using a immunoalkaline phosphatase procedure and the 9G6 antibody, HER/2-neu protein expression was found in 16 of 100 (16%) of prostate cancer specimens and protein expression correlated with high tumor grade and aneuploid DNA content. See Ross et al., supra. In another study utilizing the TA-1 antibody, overexpression of HER-2/neu protein was found to be an indicator of poor prognosis in prostate cancer and correlated with high histologic tumor grade, disease state and DNA aneuploidy. See Sadasivan et al., supra. In a study featuring analysis of a group of potential prognostic markers, HER-2/neu antigenicity was found to be a predictor of prostate cancer progression on univariate analysis and also significantly contributed to further stratification into higher risk of recurrence groups for patient subpopulations initially featuring the usually more favorable low Gleason score tumor grades. See Veltri et al., J Cell Biochem Suppl, (1994) 19:249–258.

Unfortunately, studies of HER-2/neu expression by IHC are subject to considerable technical variations. Given that most specimens are formalin-fixed, paraffin-embedded archival material, false negative staining may occur due to antigen loss. Fixation and processing protocols significantly affect the reactivity of the antigenic determinants detected by HER/2-neu antibodies such as MAB-1 and pAB-60. Ware et al., Hum Pathol, (1991) 22:254–258. Different antibodies may produce either cytoplasmic or membranous staining, be ineffective when certain fixatives are used or be impacted by temperature of the IHC reaction. Ware et al., supra. Antigen retrieval techniques featuring either enzymatic digestion or microwave irradiation contribute additional potential variables that may affect staining levels. Potential sources of error in IHC studies of HER-2/neu oncogene expression in archival breast cancer tissue samples have recently been reported. See Press et al., Cancer Res, (1994) 54:2771–2777. Substantial variation in sensitivity and specificity of commercially available HER-2/neu antibodies to detect gene amplification confirmed by Southern blotting was observed with antibodies such as the pAB-1 featuring 65% sensitivity and the 9G6, 47% sensitivity. Press et al., supra. Fixation and embedding methods similarly affect the results of IHC for HER-2/neu protein in gastric cancer. See Chiu et al., J Clin Pathol, (1994) 47:816–822. Staining interpretation problems and interobserver variability especially concerning cytoplasmic immunoreactivity for HER-2/neu protein have also been reported. See Kay et al., J Clin Pathol, (1994) 47:816–822. The present invention overcomes the above described problems associated with such variation in the immunohistochemical demonstration of HER-2/neu protein in archival tissue specimens.

SUMMARY OF THE INVENTION

A method of determining the severity of prostatic cancer includes measuring the level of amplification of the HER-2/neu gene in a sample of prostate tissue by fluorescence in-situ hybridization and comparing the measured level of amplification of the HER-2/neu gene in the sample with the level of HER-2/neu gene in normal prostate tissue.

A method for determining treatment for a patient afflicted with prostate cancer includes determining whether the number of copies of HER-2/neu gene in prostate cells from the patient exceeds four using fluorescence in-situ hybridization and aggressively treating such patients having prostate cells with five or more copies of the HER-2/neu gene.

DESCRIPTION OF PREFERRED EMBODIMENTS

Figure 1:
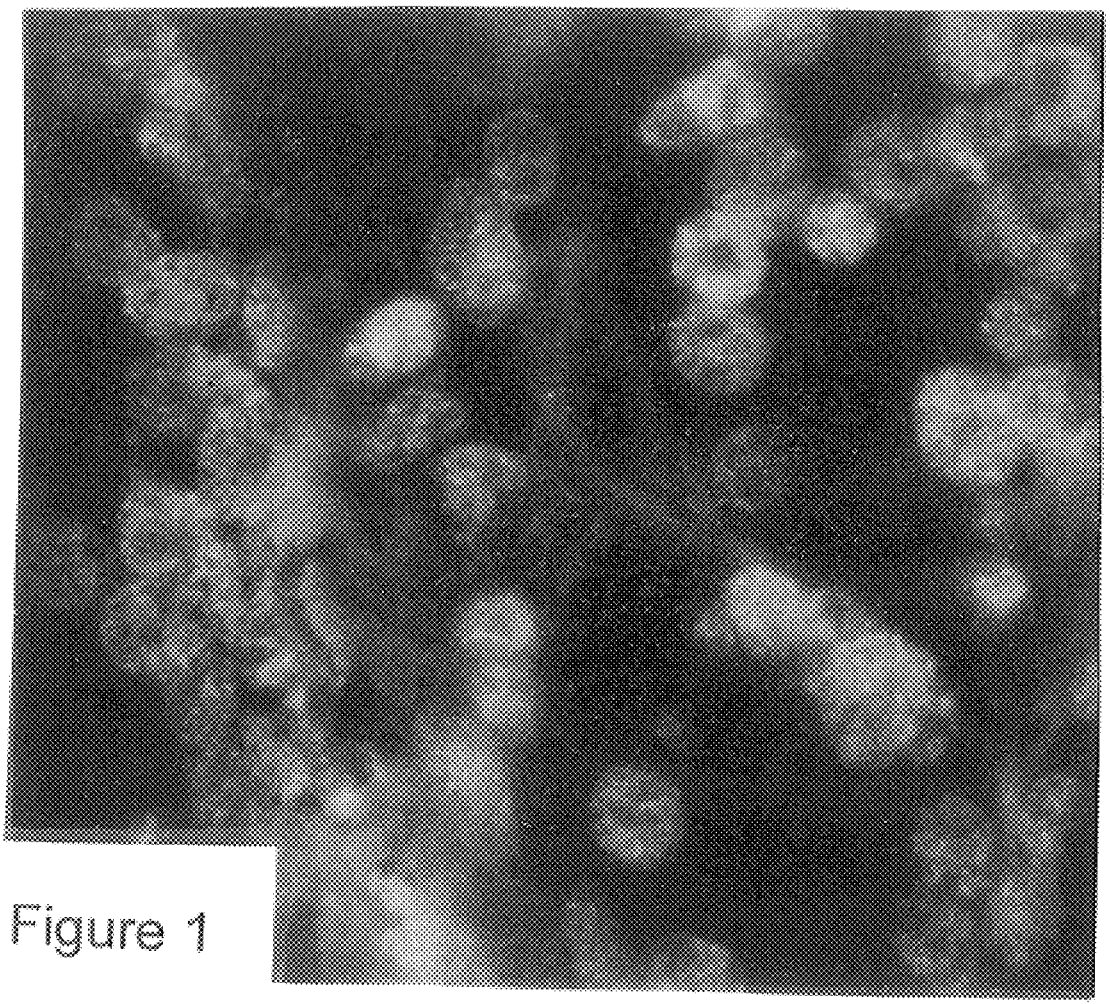
FIG. 1 is a photograph of a poorly differentiated high grade cancerous prostate tissue section showing marked amplification of the HER-2/neu gene by fluorescence in-situ hybridization.

Fluorescence in-situ hybridization (FISH) is used in accordance with the present invention to detect amplification of HER-2/neu genes in prostate tissue and provide a reliable technique for assessing the prognosis of prostate cancer which is surprisingly more effective that existing immunohistochemical (IHC) techniques. FISH detection of amplification of the HER/2-neu gene in prostate cancer tissue is compared herein with HER-2/neu protein expression as determined by IHC and correlated by logistic regression analysis with Gleason tumor grade, DNA ploidy, serum PSA and pathologic stage.

In accordance with the present invention increased copy number of the HER-2/neu gene in prostate tissues is detected using FISH techniques. The structure of the HER-2/neu gene is well known. See, e.g., King, et al., Science, 229:974–978 (1985) and Coussens et al, Science, 230:1132–1139 (1986). Detectable DNA probes capable of hybridizing to the known HER-2/neu gene sequence are constructed and labeled using conventional techniques. See, for example, PCT Application Pub. No. WO94/09022, the entire contents of which are incorporated herein by reference. Examples of labeling systems include those which incorporate digoxygenin, biotin, avidin, streptavidin and antibodies. Labeled DNA probes are then allowed to hybridize to available HER-2/neu genes and are detected using conventional fluorescence detecting techniques such as fluorescence microscopy, spectrophotometers, fluorescent plate readers and flow sorters. Fluorescent molecules can be linked directly to the DNA probe or can be linked to a binding partner for the probe or can be linked to a binding partner for a binding partner for the probe. Useful fluorescent molecules include but are not limited to fluorescein, amino coumarin acetic acid, tetramethylchodamine isocyanate, Texas Red, Cy3.0, Cy5.0, and green fluorescent protein. Signal amplification techniques known to those skilled in the art can be utilized in accordance with the present invention. Thus, signal amplification techniques such as those involving streptavidin/biotin, avidin/biotin, hapten conjugates such as digoxigenin/anti-digoxigenin, dinitophenyl and other known antibody based detection and amplification techniques are utilized herein.

Detection of increased copy number of the HER-2/neu gene in accordance with the present invention is correlated to progression of prostate cancer and devising appropriate therapy to treat the disease. The expected number of signals in a normal cell and in an unamplified tumor cell varies from 2 to 4 depending on the phase of the cell cycle. A cell with five or more signals is considered amplified. Determination of degree of severity or prognosis of prostate cancer in accordance with the present invention allows early intervention and adoption of customized treatment. Amplification of HER-2/neu correlates to a decreased chance of long term survival as well as a shortened time to relapse of the disease. Patients displaying HER-2/neu amplification can be treated more aggressively to increase chances of survival. Conversely, patients having prostate cancer with a low copy number of HER-2/neu can be treated with milder therapy to lessen or avoid adverse side effects while containing the cancer.

The following examples are included for purposes of illustrating certain aspects of the invention and should not be construed as limiting.

EXAMPLES

One hundred thirteen men ranging in ages from 49 to 88 years with a mean of 66 years who were diagnosed with prostatic adenocarcinoma and underwent radial retropubic prostatectomy between 1987 and 1996 were randomly selected from surgical pathology files. The microscopic slides from each case were reviewed and the tumors were graded and staged according to the Gleason (See Gleason, Human Pathology, 23:273–279 (1992)) and TNM (Beahrs et al., Manual for Staging of Cancer by American Joint Committee on Cancer, J.B. Lippincott Co., (1992)) systems, respectively. The pre-operative serum PSA (Tandem method, HybritechR) was obtained from review of the medical records in all cases. The pre-operative serum prostatic specific antigen levels ranged from 0.8 ng/ml to 87.8 ng/ml with a mean of 12.1 ng/ml. There was no correlation between pre-operative serum PSA level and any of the other prognostic variables or disease outcome. The mean clinical follow-up was 42 months (range 4 to 106 months). Disease recurrence was defined as a post-operative serum PSA level equal to or greater than 0.4 ng/ml.

When divided into two groups consisting of low grade cases with Gleason score six or lower (58 cases) and high grade cases with Gleason score seven or higher (55 cases), tumor grade correlated with post-operative disease recurrence (p=0.013) (Table 1). When divided into three groups consisting of low grade Gleason score 2–5; intermediate grade Gleason score 6 & 7; and high grade Gleason score 8–10, similar significant correlation of grade with disease outcome was observed on univariate analysis (p=0.0001).

EXAMPLE I

Fluorescence In-situ Hybridization

Unstained four micron formalin-fixed paraffin-embedded tissue sections were applied to silanized slides and processed according to the Oncor chromosome in-situ hybridization system (Oncor Inc., Gaithersburg, Md.). After deparaffinization in xylene and transfer through two changes of 100% ethanol, slides were allowed to air dry. The slides were then immersed for 30 minutes in 30% Oncor pretreatment solution (30% sodium bisulfite in 2xSSC (0.45 molar NaCl and 0.45 molar NaCitrate)) at 45° C. and 45 minutes in Oncor protein digesting solution (0.25 mg/ml proteinase K in 2xSSC) at 45° C. After a brief wash in 2X sodium chloride/ sodium citrate (SSC) slides were dehydrated through 100% ethanol and allowed to air dry. Oncor unique sequence digoxigenin-labeled HER-2/neu DNA probe consisting of 4 contiguous overlapping cosmid probes which create a 90 kb unbroken DNA strand (available from Oncor, Inc. Catalog Nos. P5111-BIO, P5111-DIG, P5111-B0.5, P5111-DG0.5, S8000-KIT or S8000-KIT-E) was prewarmed for five minutes at 37° C. prior to application. The amount of probe hybridization mixture was approximated according to the target area and the size of the coverslip to be placed over the tissue during hybridization (10 ul probe mixture per 22x22 mm coverslip area). Denaturation was accomplished at 69° C. for five minutes before slides were incubated overnight at 37° C. in a pre-warmed humidified chamber. Following overnight hybridization slides were again immersed in 2xSSC and pre-warmed to 72° C. for five minute stringency wash in 40 ml 2xSSC at pH 7.0 prior to detection. Fluorescein-labeled anti-digoxigenin detection reagent (10 ug/ml fluorescein anti-digoxigenin (commercially available from Boerhinger Mannheim) in a solution containing 5% nonfat dry bovine milk, 0.08% sodium azide, 0.05% NP40, 0.1 molar $NaH_2PO_4$ and 0.1 molar $K_2H_2PO_4$) was applied and a plastic coverslip placed gently for a 20 minute incubation at 37° C. in a pre-warmed humidified chamber in the dark. After careful removal of the coverslip and rinsing of excess detection compounds in 1x phosphate-buffered detergent (PBD) for three rinses at two minutes each, slides were counterstained with 18 ul of propidium iodid/antifade (1:4) and covered with a glass coverslip. Slides were evaluated for HER-2/neu gene copy number using a Zeiss Axioskop 50 fluorescence microscope.

The probe displays a single fluorescent signal at the location of each copy of the HER-2/neu gene. The expected number of signals in a normal cell and in an unamplified tumor cell varies from 2–4 depending on the phase of the cell cycle. A cell with five or more signals was considered amplified. A minimum of 100 tumor cells in each prostate carcinoma specimen were evaluated for the number of nuclear HER-2/neu signals. Amplified tumors had a minimum of 20 cells with five signals or greater per cell.

Figure 2:
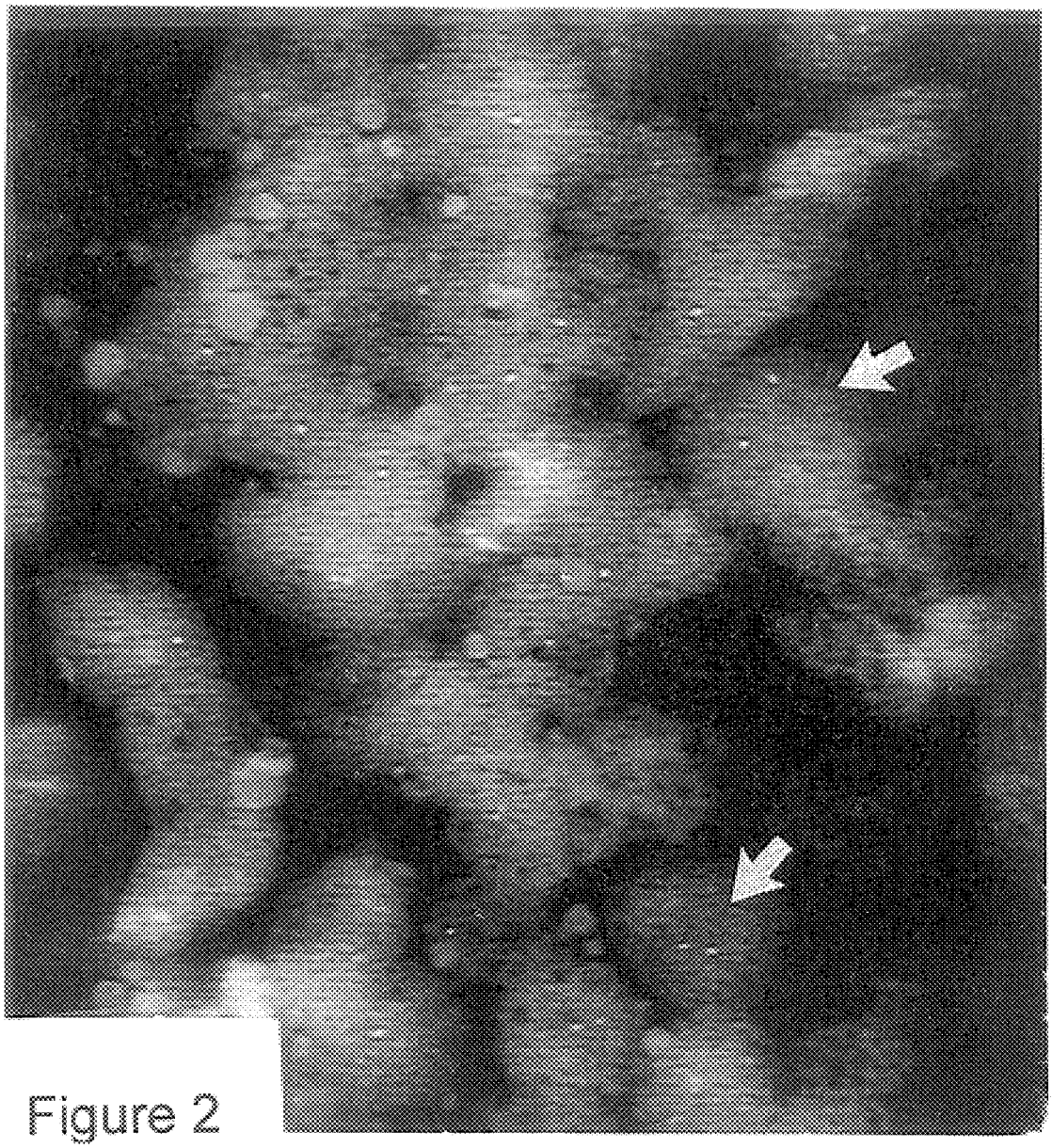
FIG. 2 is a photograph of a well differentiated prostate cancer tissue section showing several nuclei with multiple copies of the HER-2/neu gene by fluorescence in-situ hybridization.

Forty-one percent of the prostate cancers featured amplification of the HER-/2neu gene by FISH (Table 1). Tumors with gene amplification generally featured greater than 8 individual signals per nucleus in the adenocarcinomas which contrasted with the average of 2 signals per nucleus in the adjacent benign prostate tissue and stromal elements (FIG. 1). Virtually all the nuclei shown in FIG. 1, which depicts a photograph of a poorly differentiated high grade four micron paraffin-embedded formalin fixed prostate cancer tissue section, reveal flouresencence signals of HER-2/neu hybridization that are almost too numerous to count. Amplification of the HER-2/neu gene by FISH significantly correlated with high tumor grade (p=0.001) and aneuploid DNA content. (p=0.003). HER-2/neu amplification also significantly predicted post-operative disease recurrence (p=0.029) (see FIG. 2 which depicts a well differentiated prostate cancer tissue section showing several nuclei with multiple copies of the HER-2/neu gene). In patients with prostate cancer featuring HER-2/neu gene amplification by FISH, the disease was 2.3 times more likely to recur than in patients whose tumors did not feature HER-2/neu amplification. HER-2/neu gene amplification by FISH was identified in 27% of pathologic stage 2 tumors whereas pathologic stage 3 and 4 tumors featured a 59% amplification rate. This association reached near significance on univariate analysis (p=0.06). There was no correlation of HER-2/neu amplification by FISH with the pre-operative serum PSA level.

EXAMPLE II

A five micron thick tissue section from the formalin-fixed paraffin-embedded tumor tissue was stained by the Feulgen method and evaluated for total DNA content using the CAS 200 Image Analyzer (Becton Dickinson Cellular Imaging Systems, Mountainview, Calif.) as previously described. Fournier et al., supra. A DNA index of greater than 1.23 was considered non-diploid (aneuploid). Tetraploid peaks greater than 15% of the total cell population were considered non-diploid. Tetraploid peaks equal to or less than 15% of the total cell population were considered to be the $G_2M$ components of diploid cell populations.

When divided into two groups of 69 (61%) diploid cases and 44 (39%) non-diploid cases the presence of non-diploid DNA content correlated with post-operative disease recurrence on univariate analysis (p=0.016). DNA content correlated with tumor grade with 39 of 44 (89%) of the non-diploid tumors featuring high tumor grade (p=0.001).

EXAMPLE III

Immunohistochemistry

Unstained five micron sections of formalin-fixed paraffin-embedded tissue samples were deparaffinized, rehydrated and immersed in preheated 10 mM citrate buffer, pH 6.0. Slides were boiled at high power in a microwave oven for 15 minutes and allowed to stand for 30 minutes at room temperature. The slides were stained on the Ventana ES Automated Immunohistochemistry System (Ventana Medical Systems, Tucson, Ariz.) employing the Ventana indirect biotin avidin DAB detection system. Endogenous peroxidase was blocked and sections were incubated for 32 minutes at 41° C. with rabbit anit-human c-erbB-2 (HER-2/neu) at a 1:40 dilution (Dako Corp, Carpenteria, Calif.). Following primary antibody incubation, slides were sequentially incubated with universal biotinylated immunoglobulin secondary antibody, avidin horseradish peroxidase conjugate and diaminobenzidine (DAB) followed by copper sulfate enhancement. Slides were counterstained with hematoxylin. Negative control slides were included to establish background and non-specific staining of the primary and secondary antibodies and/or detection kit reagents.

A breast cancer specimen known to be positive for HER-2/neu protein expression was utilized as a positive control. Only those cases in which a majority of the tumor cells showed either an intense cytoplasmic and/or diffuse membranous staining were considered positive. Cases that were judged negative included complete lack of immunoreactivity and weak or focal staining patterns.

Figure 3:
FIG. 3 is a photograph of a cancerous prostate tissue section which was stained using immunohistochemical techniques to reveal HER-2/neu protein.

By IHC, 29% of the prostate cancers featured intense cytoplasmic or diffuse membranous immunoreactivity indicative of p185$^{neu}$ overexpression (FIG. 3). Protein overexpressed by IHC correlated with tumor grade (p=0.03), but not with ploidy (p=0.125). A trend for protein overexpression by IHC and gene amplification by FISH in the same prostate cancer specimen did not reach statistical significance (p=0.25). In addition, HER-2/neu protein overexpression by IHC did not predict post-operative disease recurrence (Table 1).

EXAMPLE IV

Analysis of Results of Examples I through III

The correlation of HER-2/neu protein expression by IHC and gene amplification status by FISH with tumor grade, DNA ploidy, pathologic stage and pre-operative serum PSA was performed using the Chi square model. A p value of less than 0.05 was considered significant. Univariate and multivariate analysis for the prediction of pathologic stage and post-operative disease recurrence by tumor grade, DNA ploidy, IHC and FISH was performed using the Cox proportional hazards model. A p value of less than 0.05 was considered significant. The impact of each prognostic variable on disease recurrence was also studied using the method of Kaplan and Meier.

When stratified into groups of PSA levels less than 10 ng/ml and PSA levels equal or greater than 10 ng/ml, there was no significant correlation of serum PSA with disease recurrence. When stratified into two pathologic stage groups of stage 2 (36% of patients) and stages 3 and 4 (64% of patients), no correlation of pathologic stage with subsequent disease recurrence was found.

On multivariate analysis using the Cox regression model, tumor grade (p=0.0001) and DNA ploidy status (p=0.001) were independent outcome predictors. The prognostic value of HER-2/neu amplification by FISH in the prediction of post-operative disease recurrence on univariate analysis (p=0.029) was reduced on multivariate analysis by either tumor grade or DNA ploidy status to near independent significance (p=0.125).

Significant association of HER-2/neu gene amplification with tumor grade and DNA ploidy and correlation with disease recurrence after radial prostatectomy is shown. Tumor grade and DNA ploidy status were independent predictors of outcome. The prognostic value of HER-2/neu gene amplification by FISH reached near independence on multivariate analysis being reduced by either grade or ploidy status. This data shows that HER-2/neu gene amplification by FISH is of significant value in predicting disease outcome, while use of IHC to detect HER-2/neu protein overexpression did not predict post-operative disease occurrence (Table 1).

TABLE 1

| Prognostic Marker | Risk Factor | % of Cases at Risk | Significant Correlation with Disease Recurrence | |
|---|---|---|---|---|
| | | | Univariate | Multi-Univariate |
| Pre-operative PSA | 10 ng/ml or higher | 19% | no | no |
| Pathologic Stage | Stage 3 or Stage 4 | 64% | no | no |
| Tumor Grade | Gleason 7 or higher | 49% | yes | yes |
| DNA Ploidy | Non-diploid | 39% | yes | yes |
| HER-2/neu Amplification by FISH | Amplified | 41% | yes | no* |
| HER-2/neu Overexpression by IHC | Overexpressed | 29% | no | no |

*Independent status of HER-2/neu amplification by FISH reduced by either grade or ploidy status to near significance (p = 0.129)

It will be understood that various modifications may be made to the embodiments disclosed herein. Therefore, the above description should not be construed as limiting, but merely as exemplifications of preferred embodiments. Those skilled in art will envision other modifications within the scope and spirit of the claims appended hereto.

What is claimed is:

1. A method of predicting disease recurrence in a prostate cancer patient comprising the steps of:
   (a) measuring the level of amplification of the HER-2/neu gene in cancerous prostate cells from the patient; and
   (b) comparing the level of amplification of the HER-2/neu gene in said cancerous prostate cells with a reference level characteristic of normal cells wherein an increased level of amplification in said cancerous cells indicates an increased risk of disease recurrence.

2. The method according to claim 1 wherein the level of amplification is measured using a detectable probe.

3. The method according to claim 2 wherein the detectable probe is a digoxygenin labeled HER-2/neu DNA probe.

4. The method according to claim 2 wherein the detectable probe is a biotinylated HER-2/neu DNA probe.

5. The method according to claim 2 wherein the detectable probe is detected with fluorescent labeled binding partner for detectable probe.

6. The method according to claim 5 wherein the labeled binding partner for the detectable probe is antibody labeled with fluorescent molecule selected from the group consisting of fluorescein, amino coumarin acetic acid, tetramethylchodomine isocyanate, Texas Red, Cy3.0, Cy5.0 and green fluorescent protein.

7. The method according to claim 3 wherein a binding partner for digoxygenin is labeled with a fluorescent molecule selected from the group consisting of fluorescein, amino coumarin acetic acid, tetramethylchodomine isocyanate, Texas Red, Cy3.0, Cy5.0 and green fluorescent protein.

8. The method according to claim 4 wherein a binding partner for biotin is labeled with a fluorescent molecule selected from the group consisting of fluorescein, amino coumarin acetic acid, tetramethylchodomine isocyanate, Texas Red, Cy3.0, Cy5.0 and green fluorescent protein.

9. The method according to claim 1 wherein a measurement of more than four copies of said gene is predictive of cancer recurrence.

* * * * *